(12) United States Patent
Larson et al.

(10) Patent No.: US 7,305,264 B2
(45) Date of Patent: Dec. 4, 2007

(54) BONE CANCER PAIN MANAGEMENT UTILIZING ULTRASOUND

(75) Inventors: Eugene A. Larson, Lummi Island, WA (US); Perry W. Kaminski, Stehekin, WA (US); Yu-Chi Chu, Brier, WA (US)

(73) Assignee: UST, Inc., Everett, WA (US)

( * ) Notice: Subject to any disclaimer, the term of this patent is extended or adjusted under 35 U.S.C. 154(b) by 90 days.

(21) Appl. No.: 10/994,421

(22) Filed: Nov. 22, 2004

(65) Prior Publication Data

US 2005/0113872 A1    May 26, 2005

Related U.S. Application Data

(60) Provisional application No. 60/524,200, filed on Nov. 21, 2003.

(51) Int. Cl.
*A61B 6/00*    (2006.01)

(52) U.S. Cl. ............. 600/427; 600/439; 600/459; 601/2

(58) Field of Classification Search ............ 600/427, 600/439, 459; 601/2, 3
See application file for complete search history.

(56) References Cited

U.S. PATENT DOCUMENTS

| 4,708,127 A | * | 11/1987 | Abdelghani | ............ 601/2 |
| 5,727,556 A | * | 3/1998 | Weth et al. | ............ 600/439 |
| 5,807,285 A | * | 9/1998 | Vaitekunas et al. | ............ 601/2 |
| 6,428,477 B1 | * | 8/2002 | Mason | ............ 600/437 |

* cited by examiner

*Primary Examiner*—Ruth S. Smith
(74) *Attorney, Agent, or Firm*—Robert L. McDowell

(57) ABSTRACT

Noninvasive pain treatment of skeletal cancer metastases in cancer patients utilizing planar or focused ultrasound. The ultrasound energy preferably targets at the Periosteum or immediate soft-bone-tissue interface, where local sensory pain receptors are directly affected by the growing tumor, to generate heat to destroy local sensory pain receptors so as to interrupt or block the pain feedback pathway to the central nervous system.

15 Claims, 2 Drawing Sheets

BONE CANCER PAIN MANAGEMENT UTILIZING ULTRASOUND

This application claims the benefit of U.S. Provisional Patent Application No. 60/524,200 filed Nov. 21, 2003.

FIELD OF THE INVENTION

The present invention utilizes planar or focused ultrasound applied transcutaneously to reduce bone pain of skeletal metastases in cancer patients.

BACKGROUND OF THE INVENTION

Bone metastasis is one of the most common causes of pain in cancer patients. In the United States, it is estimated that of 1.4 million patients who will be diagnosed with cancer, 30% to 70% will develop skeletal metastases. In one study, the prevalence of pain was shown to be 55% of ambulatory patients, and 46% of those patients reporting pain received inadequate analgesics. Each year there is estimated 150,000 painful bone metastases cases from advanced lung, breast, and prostate cancer in the United States.

Bone cancer is a growth found in any part of the bone. Most bone cancers develop predominantly from bone, cartilage, muscle, fibrous tissue, fatty tissue or nerve tissue. Primary bone cancer originates in the bone itself. The most common primary malignancies that metastasize to the bone are breast, kidney, lung, and prostate. The most common sites of metastasis are the vertebrae, pelvis, and long bones. Secondary bone cancers, which are more common than primary cancers, spread from other cancerous cells in the body. Primary and Secondary types of bone cancer are described below.

Primary Bone Cancer:
A. Osteosarcome: the most common type of primary bone cancer, develops in new tissues of growing bones, particularly the knees, upper legs, upper arms. Patients often children and young people between 10 and 25 years old.
B. Ewing's Sarcoma: this sarcoma begins in immature nerve tissue in the bone marrow of the body's large bones, i.e. pelvis, upper legs, ribs and arms. Ewing's sarcoma affects children and young adults.
C. Chondrosarcoma: this usually arises in the cartilage, soft connective tissue of the pelvis, upper legs and shoulders. This type of malignancy most frequently affects adults over 50 years old.

Secondary Bone Caner:
It is more common than primary bone cancer and usually occurs later in life. Cancers that tend to spread rapid to bone are breast, lung, prostate, thyroid, and kidney. Pain usually results when a tumor pushes on bones, nerves, or other organs in the body.

Current pain control treatments include:
A. Surgery to remove all or part of the affected bone.
B. Chemotherapy involves the use of drugs that target the given tumor cells. Significant side effects are problematic.
C. Radiation Therapy utilizes X-ray or other radioactive source to destroy the development of abnormal cells. Similar to chemotherapy, radiation may impact normal tissues.
D. Hormone Therapy is used to stem secondary bone cancers of the prostate and breast.
E. Analgesic Drugs: radiopharmaceuticals, bisphosphonates, calcitonin and others to treat pain via blocking pain pathways or inhibit local growth factors.
F. Radiofreqency ablation on benign lesion of bone (osteoid osteoma) targeting at nidus, where composed of a variably calcified meshwork of bony trabeculae on a background of fibrous, vascular, and nerve tissue. Percutaneous RF ablation treats the margin of the lesion at the soft-tissue-bone interface for pain reduction.

The above therapies may have serious side effects and limitations can include:
A. Poor therapeutic response or toxicity from chemotherapy.
B. Intolerable analgesic related side effects may develop with increasing analgesic doses.
C. Limited patients are suitable for radiation therapy because of radiation insensitivity of the neoplasm or limitations of radiation dose that can cause damage to normal structure and healthy cells.

Although terminal patients undergo combinational treatment plan, the current treatments are ineffective to relieve pain.

Tumor metastasis to bone is associated with bone destruction and new bone formation. Bone pain often results from the tumor impinging on nerve tissue, disrupting normal bone remodeling process, and displacing bone. The pain is usually described as a deep, aching over the site of the involved bone.

The sensory receptors within the human body are sensitive to tissue damaging or stimuli that are prevalent in skin, muscle, joint, bone and other connective tissues. Those nociceptors (sensory receptors) are sensitive to response to mechanical, thermal, and chemical cutaneous stimuli. It is believed that nociceptor sensitization is a physiologic mechanism of persistent pain. Once nociceptors activated locally, it transduces chemical, mechanical, or thermal stimuli into afferent impulses that enter the nervous system to the brain for pain perception. Particularly, A-δ mechanoreceptors and C-nociceptors appear to be localized to connective tissue between muscle fibers and in blood vessel walls or tendons, and in the joint capsule and periosteum.

Particularly, numerous studies have shown that the periosteum, which is comprised of fibrous connective tissue sheath that covers the external surface of all bones, is densely innervated by both sensory and sympathetic fibers. Nerves are distributed to the Periosteum and accompany the nutrient arteries into the interior of the bone. Fine nerve endings are found in bone marrow, periosteum, cortex, and associated muscles and ligaments. The prevailing opinion is that bone pain arises predominantly from the densely innervated periosteum, where is the area of interest for ablating local pain receptors utilizing ultrasound to reduce bone pain.

SUMMARY OF THE INVENTION

The present invention is directed to noninvasive or minimal invasive pain treatment of skeletal cancer metastases in cancer patients utilizing planar or focused ultrasound. The ultrasound energy preferably targets at the Periosteum or immediate soft-bone-tissue interface, where local sensory pain receptors are directly affected by the growing tumor, to generate heat to destroy local sensory pain receptors so as to interrupt or block the pain feedback pathway to the central nervous system.

DETAILED DESCRIPTION OF THE PREFERRED EMBODIMENTS

The present invention is directed to noninvasive pain treatment of skeletal cancer metastases in cancer patients utilizing planar or focused ultrasound.

A preferred method of noninvasive pain treatment includes interrupting the activation of nociceptors and blocking pain feedback pathway. A preferred method is described below.

Figure 1:
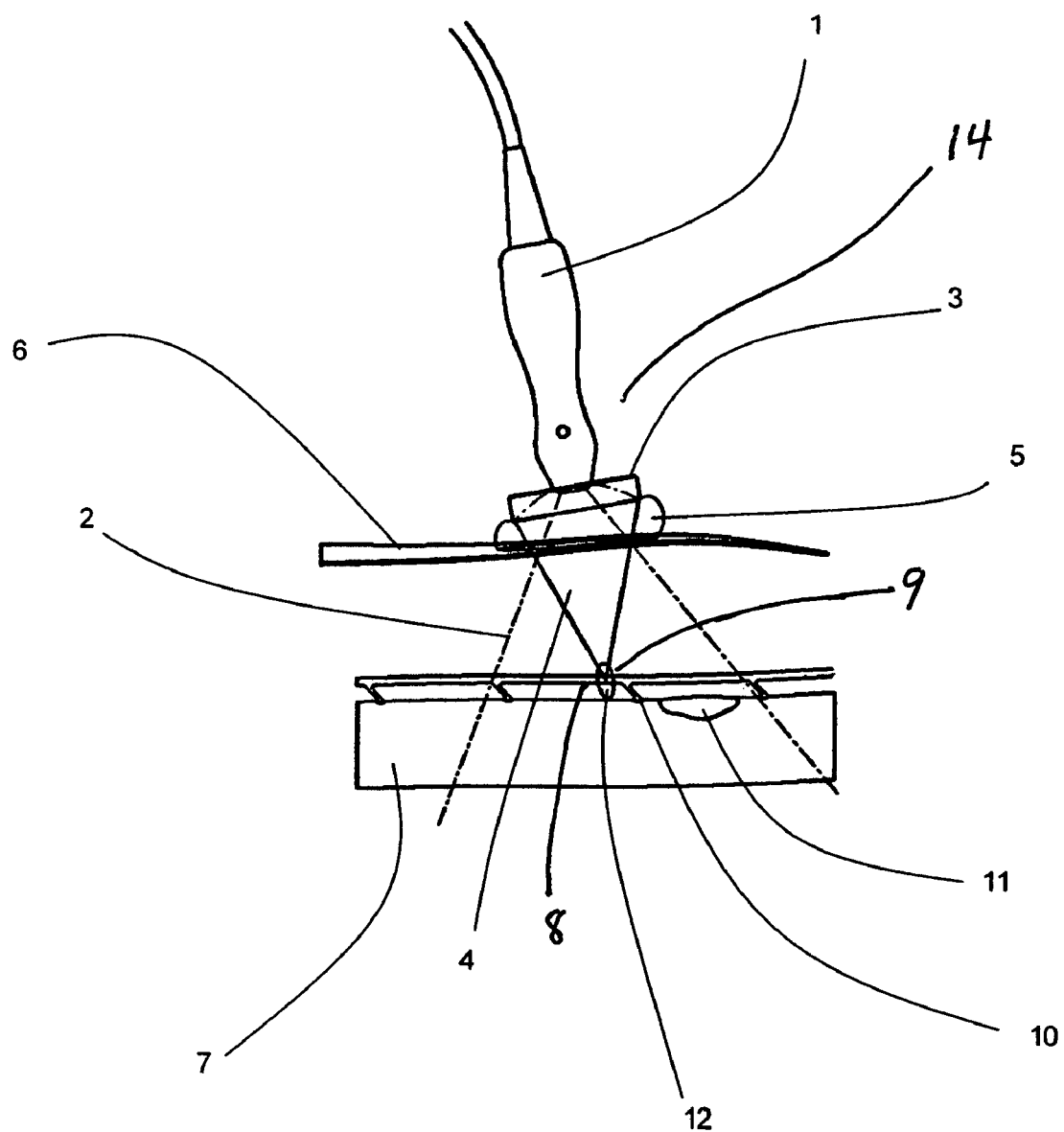
FIG. 1 illustrates a single unit comprising imaging and therapy transducers for treating nerves.

One or more therapeutic target sites 9 (FIG. 1) are located by use of an imaging modality which, preferably, also displays the location of the bone cancer site 11. The imaging guided system can be Computerized Axial Tomography (CT), Magnetic Resonance (MR), X-Ray, ultrasound, such as diagnostic ultrasound 1 or other imaging modality.

Utilizing a planar or focused ultrasound transducer 3 with frequencies range from 0.75 to 7.0 MHz, the ultrasound 4 is applied to the patient transcutaneously with acoustic coupling to the skin 6 using, for example, a water path, gel couplant or hydrogel 5. The transcutaneous coupling may utilize a suitable acoustic delay member, such as a water column or a specified geometric shape hydrogel (e.g. a hydrogel cone).

Local heating of the nerve endings at the Periosteum (about 45° C. to 67° C.) is generated utilizing acoustic power (preferably ranging from 5 to 1000 W/cm$^2$) thereby resulting in destruction of the nerve tissue 8 proximal to a bone cancer site 11. High Intensity Focused Ultrasound (HIFU) is the preferred method for generating the necessary heat at the nerve endings.

Preferably, the ultrasound is delivered to the target site using the image-guided system 2 to identify and mark therapeutic sites. It is also preferred that the ultrasound transducer is operated with the image-guided system to allow both treatment and monitoring functions. If the target site 9 can be readily identified when viewed, no image guidance system is necessary as visual guidance is acceptable in this instance. Preferably, when placing a therapeutic lesion in the region of interest, a hyperechoic spot 12 may be created due to the production of microbubbles by HIFU, and this hyperechoic spot 12 can be utilized in the ultrasound image to monitor the progress of the pain treatment therapy.

Alternatively, image guided therapeutic HIFU may be utilized to destroy nerves in the Periosteum at a predetermined location 10 on the bone 7 and thereby block or reduce pain transmission from the bone.

If desired, the acoustic intensity can be controlled such that damage to the nerves is sub-lethal tissue and/or cellular damage thereby causing a temporary and reversible loss in nerve conduction. In such instances, the sub-lethal damage is preferably directed to the myelin sheath which surrounds individual nerve axons. Heating of the nerves to within the range of about 40° C. to about 45° C. is believed to be satisfactory to accomplish the sub-lethal damage.

Figure 2:
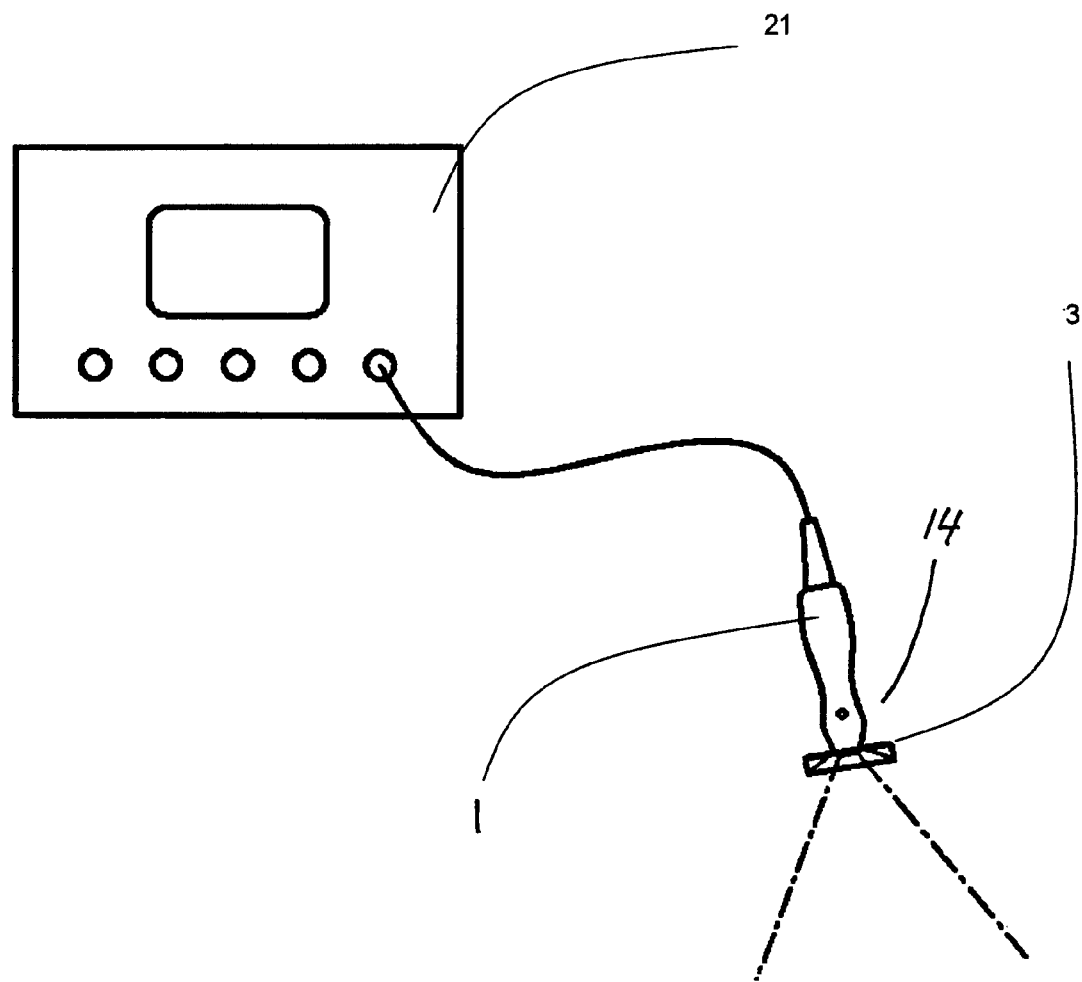
FIG. 2 illustrates a control interface for controlling imaging and therapy emitted from the single unit of FIG. 1.

The imaging and therapy transducers 1, 3 used to treat the nerves 8 may be separate units, but connected by a rigid construction or the imaging and therapy transducers 1, 3 may be incorporated into a single unit 14, so that imaging and therapy can be accomplished with the same control interface 21 (FIG. 2).

While the invention has been described with reference to preferred embodiments it is to be understood that the invention is not limited to the particulars thereof. The present invention is intended to include modifications which would be apparent to those skilled in the art to which the subject matter pertains.

What is claimed is:

1. A method for reducing pain due to bone cancer, said method comprising:

targeting a region of interest with an imaging modality comprising ultrasound;

emitting therapeutic ultrasound energy from an ultrasound radiating surface and focusing the emitted therapeutic ultrasound energy on the region of interest;

producing tissue damage to nerves supplying the region of interest;

wherein imaging and therapy transducers are incorporated into a single unit whereby imaging and therapy can be accomplished with the same control interface, and wherein the emitted ultrasound energy comprises HIFU and said focusing the emitted ultrasound causes the formation of microbubbles in the region of interest, said microbubbles producing a hyperechoic spot on said imaging modality with said hyperechoic spot being utilized in the imaging modality to monitor the progress of the nerve tissue damage.

2. The method of claim 1 wherein the ultrasound radiating surface is located external to the body and the ultrasound energy is delivered extracorporeally.

3. The method of claim 1 wherein the damage to the nerves is sub-lethal tissue and/or cellular damage, causing a temporary, reversible loss in nerve conduction.

4. The method of claim 3 wherein the sub-lethal damage the nerves is to the myelin sheath surrounding an individual axon.

5. The method of claim 3 wherein the applied acoustic intensity is delivered at a level sufficient to terminate nerve conduction, but not sufficient to irreversibly damage the surrounding tissue.

6. The method of claim 1 wherein the emitted ultrasound energy produces lethal tissue damage to predetermined nerves proximal to the region of interest.

7. The method of claim 1 wherein coupling between the HIFU transducer and a patient is accomplished with a water path, a gel couplant, or a hydrogel.

8. An apparatus for use in reducing pain due to bone cancer, said apparatus comprising:

ultrasound emitting means having an ultrasound radiating surface adapted for placement non-invasively on a patient's skin;

said ultrasound emitting means being selectively operable to emit a selected level and/or frequency of ultrasound from said ultrasound radiating surface to a taraet site proximal to a bone cancer site;

wherein said level and/or frequency of said ultrasound is selected to produce sub-lethal or lethal nerve damage at the target site proximal to the bone cancer site and is further selected to produce a hyperechoic spot at the target site;

an imaging means for locating and displaying the bone cancer site, said imaging means monitoring the hyperechoic spot as an indicator of pain reduction progress;

wherein the ultrasound emitting means and the imaging means are incorporated into a single unit with the same control interface.

9. The apparatus of claim 8 wherein said imaging means comprises one of Computerized Axial Tomography, magnetic resonance, X-ray or ultrasound.

10. The apparatus of claim 9 wherein the imaging ultrasound comprises diagnostic ultrasound.

11. The apparatus of claim 8 wherein the nerve damage is lethal nerve damage located at the periosteum, or the immediate soft-bone-tissue interface or the myelin sheath.

12. The apparatus of claim 8 wherein the nerve damage is sub-lethal nerve damage located at the myelin sheath.

13. The apparatus of claim 8 wherein the ultrasound comprises planar or focused therapeutic ultrasound.

14. The apparatus of claim 13 wherein said ultrasound operates at a frequency range of 0.75-7.0 MHz.

15. The apparatus of claim 13 wherein said ultrasound comprises High Intensity Focused Ultrasound.

* * * * *